US012672840B2

(12) United States Patent (10) Patent No.: US 12,672,840 B2
Kuenen et al. (45) Date of Patent: Jul. 7, 2026

(54) SYSTEM AND METHOD FOR ROBUST FLOW MEASUREMENTS IN VESSELS

(71) Applicant: KONINKLIJKE PHILIPS N.V., Eindhoven (NL)

(72) Inventors: Maarten Petrus Joseph Kuenen, Veldhoven (NL); Brian Brand Antonius Johannes Bloemendal, Helenaveen (NL); Arjen Van Der Horst, Tilburg (NL)

(73) Assignee: KONINKLIJKE PHILPS N.V., Eindhoven (NL)

( * ) Notice: Subject to any disclaimer, the term of this patent is extended or adjusted under 35 U.S.C. 154(b) by 602 days.

(21) Appl. No.: 17/794,648

(22) PCT Filed: Jan. 20, 2021

(86) PCT No.: PCT/EP2021/051090
§ 371 (c)(1),
(2) Date: Jul. 22, 2022

(87) PCT Pub. No.: WO2021/148416
PCT Pub. Date: Jul. 29, 2021

(65) Prior Publication Data
US 2023/0142143 A1 May 11, 2023

(30) Foreign Application Priority Data
Jan. 23, 2020 (EP) ..................................... 20153274

(51) Int. Cl.
*A61B 8/06* (2006.01)
*A61B 8/00* (2006.01)
*A61B 8/12* (2006.01)

(52) U.S. Cl.
CPC .................. *A61B 8/06* (2013.01); *A61B 8/12* (2013.01); *A61B 8/4245* (2013.01); *A61B 8/488* (2013.01); *A61B 8/5207* (2013.01); *A61B 8/445* (2013.01)

(58) Field of Classification Search
None
See application file for complete search history.

(56) References Cited

U.S. PATENT DOCUMENTS

| | | | |
|---|---|---|---|
| 4,259,870 A | 4/1981 | McLeod | |
| 6,601,459 B1 | 8/2003 | Jenni | |

(Continued)

FOREIGN PATENT DOCUMENTS

| | | | |
|---|---|---|---|
| EP | 3613350 A1 | 2/2020 | |
| WO | WO-2018065266 A1 * | 4/2018 | ........... A61B 5/0215 |

OTHER PUBLICATIONS

Poelma et al., "Ultrasound Imaging Velocimetry: a review". Exp Fluids 2017 58:3, pp. 1-28. (Year: 2017).*

(Continued)

*Primary Examiner* — Yi-Shan Yang

(57) ABSTRACT

The invention provides a system and a method for calculating flow parameter based on a plurality of ultrasound reflections received from a plurality of distances along the vessel. A first flow parameter at a first location and a second flow parameter at a second location is calculated respectively from a first ultrasound signal associated to ultrasound reflection at the first location and from the second ultrasound signal associated to ultrasound reflection at the second location. A composite flow parameter is computed based on the first flow parameter and the second flow parameter, which is then output to a user interface.

13 Claims, 9 Drawing Sheets

(56)     References Cited

U.S. PATENT DOCUMENTS

| 2017/0188993 A1* | 7/2017 | Hamilton | A61B 8/4218 |
| 2021/0338193 A1 | 11/2021 | Kuenen | |
| 2023/0000469 A1* | 1/2023 | Prus | A61N 7/00 |

OTHER PUBLICATIONS

International Search Report and Written Opinion of PCT/EP2021/051090, dated Apr. 13, 2021.

* cited by examiner

SYSTEM AND METHOD FOR ROBUST FLOW MEASUREMENTS IN VESSELS

CROSS-REFERENCE TO PRIOR APPLICATIONS

This application is the U.S. National Phase application under 35 U.S.C. § 371 of International Application No. PCT/EP2021/051090, filed on Jan. 20, 2021, which claims the benefit of European Patent Application No. 20153274.4, filed on Jan. 23, 2020. These applications are hereby incorporated by reference herein.

FIELD OF THE INVENTION

This invention relates to system for measuring flow and method of measuring flow in anatomical structures.

BACKGROUND OF THE INVENTION

Assessing the hemodynamic significance of cardiovascular and peripheral vascular disease by intravascular flow measurement has been beneficial to guide treatment of circulatory disease. Especially, for the coronary arteries large clinical trials have proven that decision-making based on pressure and flow measurements improves clinical outcome compared to the use of angiography alone. Flow measurements are particularly valuable in the case of non-obstructive coronary artery disease, i.e. angina complaints without visible obstructions in the large arteries. Furthermore, flow measurements in other areas like peripheral vascular disease can be beneficial to quantify the effect of atherosclerosis on the blood supply to the feet and help defining the end point of endovascular treatment (e.g. stent, atherectomy). Additionally, in the field of oncological interventions, blood flow monitoring during embolization is potentially helpful in assessing the degree of embolization and in preventing embolization of healthy tissue (e.g. in transarterial chemoembolization).

Guidewires for blood flow velocity measurement have been developed, which are equipped with a single element ultrasound transducer at their distal end. With these devices, an ultrasound pulse can be sent and received. Blood flow velocity can be derived by analyzing the received signals, e.g. by pulsed-wave Doppler processing.

One of the difficulties is the generally limited signal to noise ratio (SNR) and robustness of the measurement, which may lead to inaccurate results, in particular when the guidewire is not optimally positioned within the vessel.

Accordingly, there is a need for improvement of the robustness of flow measurements in anatomic structures, such as vessels.

SUMMARY OF THE INVENTION

According to examples in accordance with an aspect of the invention, an apparatus is provided for flow measurements in a vessel, comprising a processor configured to:

obtain a first ultrasound signal and a second ultrasound signal from an ultrasound transducer of an interventional device, wherein the first ultrasound signal is associated to ultrasound reflection at a first location $(z_1)$ in the vessel separate from a location of the ultrasound transducer and the second ultrasound signal is associated to ultrasound reflection at a second location $(z_2)$ in the vessel separate from the location of the ultrasound transducer;

ascertain a first flow parameter at the first location and a second flow parameter at the second location based on the first and second ultrasound signals, respectively;

ascertain a composite flow parameter based on the first flow parameter and the second flow parameter;

output to a user interface the composite flow parameter.

The interventional device, which may be any intravascular device (e.g. guidewire, catheter) or interventional needle (e.g interventional needle for percutaneous access of vessels), comprises an ultrasound transducer at its distal portion that is configured for introduction into the anatomy of the patient. The apparatus may be configured to generate a plurality of electrical pulses to transmit to the ultrasound transducer, which converts the electrical pulses to ultrasound pulses that propagate into the anatomy (e.g vessel, heart chamber) or a medium within the anatomy (e.g. blood) and the ultrasound transducer receives a plurality of echo signals, which are reflected ultrasound pulses or ultrasound waves. Upon the impinging ultrasound pulses ultrasound echo signals originate from the first measurement location, at a distance from the transducer, thus separate or distinct from the location of the ultrasound transducer, and ultrasound echo signals originate from a second measurement location separate or distinct from the location of the ultrasound transducer. The first and second locations are distinct, thus separated by a distance from each other. In some embodiments the separation is in the direction of transmission/reception of the ultrasound pulses that are emitted/received by the transducer. The processor is configured to compute a first flow parameter at the first location and a second flow parameter at the second location from the received echo signals, and subsequently to compute a composite flow parameter based on the first flow parameter and the second flow parameter. The benefit of the composite flow parameter is that it is less dependent on the position and/or orientation of the ultrasound transducer with respect to the anatomical structures. Furthermore, the computation of the composite parameter can improve signal quality by reducing variance in the flow parameter, which improves the robustness of the flow velocity measurement in general.

In some embodiments, the flow parameter is flow velocity parameter, e.g. Doppler spectrum (magnitude and/or power), instantaneous peak velocity, average peak velocity, and the composite flow parameter is composite flow velocity parameter. In other embodiments, the flow parameter is volumetric flow and the composite flow parameter is composite volumetric flow.

In an embodiment of the apparatus, the first location comprises a first distance interval and the second location comprises a second distance interval. The first and second distal intervals are selectable by the user, for example by user interface input, or can be predefined based on clinical application benefiting from the flow measurement, e.g. in heart chamber where the flow is less disturbed by the presence of the interventional device and the anatomic structure like the heart wall is further away from the ultrasound transducer, the distance intervals can be selected to be larger than in a coronary application, where in small vessels the presence of the interventional device disturbs the flow in its immediate proximity and where the vessel walls are closer to the ultrasound transducer. The benefit of having distance intervals for the respective locations is that computation of the flow parameters are performed for sampling distances or sampling volumes defined by the respective distance intervals, leading to increased reliability of the flow measurements. Furthermore, having distance intervals for the respective locations provides additional agility in the computation of the composite flow parameter, by dynamically adjusting the distal intervals or their contribution to the composite flow parameter, which may be required or caused by changes in the environment (e.g. due to a beating heart).

In some embodiments the first and second distance intervals are spatially aligned along the ultrasound transmission and/or reception axis of the ultrasound transducer. In an embodiment the first and second distance intervals are subsequent distance intervals and in an alternative embodiment the first and second distance intervals partially overlap. Whether the first and second distal intervals partially overlap or not, are selectable by the user, for example by user interface input, or can be predefined based on clinical application benefiting from the flow measurement. In general, having adjacent or partially overlapping sampling volumes assures continuity of measurement values used for computation of the composite flow parameter, thus without having major discrepancy between measurements values, which would appear in case of two further apart sampling distances or volumes. Advantageously, this offers greater flexibility in selecting the respective distance intervals.

In any of the disclosed embodiments of the apparatus the processor can be configured to compute the composite flow parameter based on a first weighting factor applied to the first flow parameter and a second weighting factor applied to the second flow parameter. Weights or weighting factor values can vary for example as function of any of: distance range, time, Doppler frequency, Doppler magnitude spectrum data, and context information (e.g. user input or input from additional imaging sources). The benefit is that clinical application specificity and robustness can be optimized for the composite flow parameter calculation.

In some embodiments the first and second weighting factors are ascertained automatically by the processor. The weighting factors can be ascertained based on correlation among the Doppler magnitude spectra for the respective distance intervals, preferably based on optimization by using minimum variance of the combined Doppler magnitude spectrum over the distance intervals. This optimally reduces the variance in the composite Doppler magnitude spectrum, which improves the flow velocity measurement robustness in general.

In alternative embodiments the weighting factors are ascertained based on the gradient of the Doppler magnitude spectra for the respective distance intervals. This is advantageous in particular when the objective is to derive the instantaneous maximum blood flow velocity that is present in the blood vessel, such as instantaneous peak velocity (IPV), from the Doppler magnitude spectrum. This is for example the case in Doppler ultrasound coronary flow reserve (CFR) measurements. The confidence with which the IPV is estimated depends on the difference in intensity between the desired blood flow signal and the noise floor. In an embodiment, this confidence may be quantified by the difference or gradient in the Doppler magnitude spectrum over frequency at the detected IPV. One may evaluate to what extent the individual Doppler magnitude spectra contribute to the difference or gradient of the composite Doppler magnitude spectrum, and optimize the weights such that this difference or gradient is maximized. This optimization may be implemented as an iterative process in which weights are initialized (e.g. unity weights). The iterative process starts by calculating the composite Doppler magnitude spectrum. Next, the IPV is evaluated and the difference or gradient of the individual magnitude spectra at the IPV is evaluated. The weights are optimized based on the difference or gradient values, and the iterative process goes back to its start. The iteration process may stop whenever a satisfactory difference or gradient value of the composite Doppler magnitude spectrum is found, when the increase in this difference or gradient value is below a threshold, when the absolute or relative change in IPV is below a threshold, when the weights hit upper/lower limit of allowed values, when a local optimum is found given a certain step size, or when a maximum number of iterations is reached.

In yet a further alternative embodiment the processor is configured to receive position and/or orientation information of the ultrasound transmission and/or reception axis of the ultrasound transducer with respect to the anatomy of a vessel for which flow measurement is performed, and the processor is further configured to compute the weighting factors based on the position and/or orientation information. This allows dynamically registering the distance of the blood flow velocity measurement to the position of the blood vessel, thereby improving the robustness of the blood flow velocity measurement particularly in the event of motion.

In any of the embodiments of the apparatus the processor may be configured to compute the composite flow parameter based on averaged Doppler magnitude spectra after scaling the different Doppler magnitude spectra per respective distance intervals such that the noise floor values over the respective distance intervals is brought to substantially equal values. This minimizes the noise variance in the averaged Doppler magnitude spectrum and emphasizes those distance intervals featuring the highest velocity signal energy.

In any of the embodiments of the apparatus the processor may be configured to obtain a further plurality of ultrasound signals associated to ultrasound reflections at respective plurality of locations at respective distances from the ultrasound transducer, wherein the plurality of locations are spatially aligned along the ultrasound transmission and/or reception axis of the ultrasound transducer. Covering the further plurality of locations allows for selection and or weighting in order to maximize signal quality (e.g. to maximize the confidence/reliability in the estimated IPV).

According to a further aspect of the invention a system is provided, comprising: an apparatus according to any of the embodiments according to the invention;
    the interventional device including an ultrasound transducer on its distal portion; and the user interface for
        outputting the composite flow parameter.

In a further aspect of the invention a method of flow measurement is provided, comprising:
    obtaining a first ultrasound signal and a second ultrasound signal from an ultrasound transducer of an interventional device, wherein the first ultrasound signal is associated to ultrasound reflection at a first location in the vessel separate from a location of the ultrasound transducer and the second ultrasound signal is associated to ultrasound reflection at a second location in the vessel separate from the location of the ultrasound transducer;
    ascertaining a first parameter at the first location and a second flow parameter at the second location based on the first and second ultrasound signals, respectively;
    ascertaining a composite flow parameter based on the first flow parameter and the second flow parameter;
    outputting to a user interface the composite flow parameter.

The method may comprise in optional embodiments the processor carrying out operations that are mentioned for any of the embodiments of the apparatus according to the invention.

In yet a further aspect of the invention a computer program is provided, wherein the computer program code means of the computer program is adapted, when said computer program run on a computer, to implement any of the methods according to the invention on any of the systems according to the invention.

These and other aspects of the invention will be apparent from and elucidated with reference to the embodiments described hereinafter.

BRIEF DESCRIPTION OF THE DRAWINGS

Examples of the invention will now be described in detail with reference to the accompanying drawings, in which.

DETAILED DESCRIPTION

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. The invention will be described with reference to the Figures.

Figure 1:
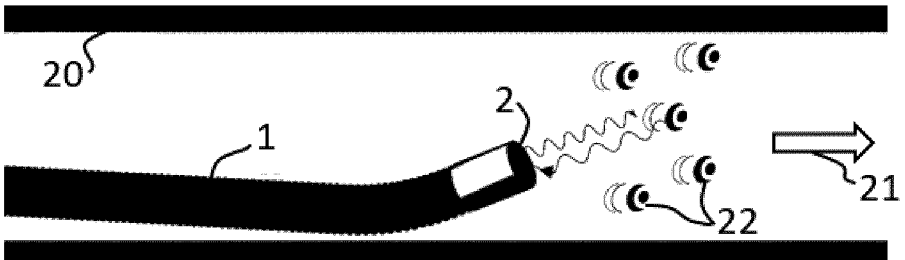
FIG. 1 shows exemplarily an interventional device in a vessel.

To assess blood flow, interventional devices 1 are equipped with a single element ultrasound transducer 2 at their distal portion, as illustrated in FIG. 1. An ultrasound pulse is sent and received by the ultrasound transducer 2. From the analysis of the received signals, the blood flow velocity in a specific sampling area can be deduced. Intravascular devices, such as catheter and guidewires, are interventional devices that are in particular used for measurement of blood flow velocity in various vessels 20 in the circulatory system of a patient, however other interventional devices such as interventional needles can be equipped with ultrasound transducer for detecting vessels in the anatomy of the patient based on ultrasound Doppler measurements. Philips Volcano commercializes Doppler ultrasound guidewires, such as the FloWire and the ComboWire, generally used for blood flow velocity measurements in the coronary arteries.

In ultrasound Doppler and imaging, the ultrasound transducer 2 transmits bursts at a controlled rate, the pulse repetition frequency (PRF). After transmission of each pulse, the transducer switches into receive mode and a so-called radiofrequency (RF) line can be measured after each pulse transmission, which comprises the echo signals caused by reflection of the transmitted pulse by blood cells 22, which move substantially in the direction 21 as exemplarily and schematically indicated in FIG. 1, however, the blood cells may move substantially in opposite direction of the arrow, depending on the site of introduction of the interventional device in the vessel. These together form one acquisition, in which the RF line is measured over a timescale of several microseconds. It is typically a band-limited signal with frequency content mainly at the transmitted pulse frequency. The time (referred to as "fast time") between transmission and reception for each acquisition, reflects the distance between transducer and a scatterer, twice the distance divided by the ultrasound propagation velocity. The complex amplitude (and/or phase) of the signal varies as function of time and is used in ultrasound imaging (amplitude) and Doppler (phase) applications. In an example the PRF is provided by a hardware such as an ultrasound console connected to the interventional device. In some example the PRF is 50 kHz.

Figure 2:
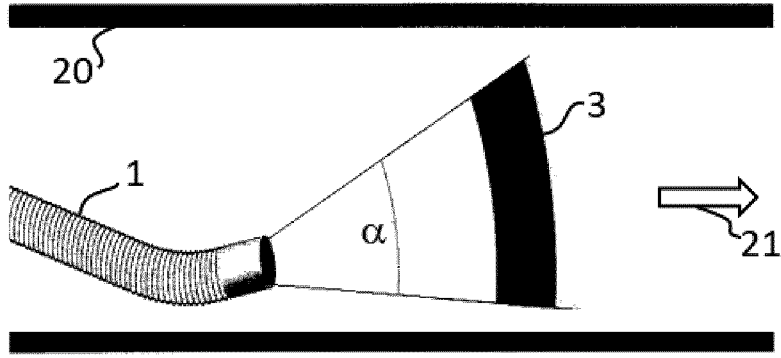
FIG. 2 shows an example of a sampling volume for flow measurement in a vessel.

In Doppler application, the desired information is extracted over successive acquisitions, which provide the complex amplitude signal, so-called in-phase and quadrature (IQ signal) as function of distance ("fast time") and acquisition time ("slow time"). The so-called "Doppler signal" is obtained by sampling this complex signal in one distance range 3, illustrated in FIG. 2, as function of only the slow-time. In spectral Doppler, the frequency content of this Doppler signal is displayed. In practice, this is implemented by a Fourier transform of the complex amplitude signal over a fixed number of slow-time samples (or pulse transmissions). The distribution of frequencies in the Doppler signals, as obtained by the magnitude or power spectrum of the Doppler signal, relates analytically (i.e. without calibration) to the distribution of flow velocities within the sampling volume by the Doppler equation $$f_D = -\frac{2v\cos(\theta)}{c} f_c.$$

The Doppler frequency $f_D$ depends on the axial velocity v, the ultrasound propagation velocity c (assumed to be constant in blood, 1566 m/s), the ultrasound frequency $f_c$ (determined by the system, for example 12 MHz), and the angle $\theta$ ("Doppler angle") between the ultrasound beam and the flow. For the intravascular flow measurement, $\theta$ is assumed to be negligible, thus $\cos(\theta)=1$.

In the following, processing routines used in spectral Doppler are summarized:

demodulation (e.g. phase-quadrature demodulation) converts the RF signal to the IQ signal;

clutter filtering (e.g. by a high-pass filter) is used to reduce low-frequency content in the Doppler signal, which—depending on the application—mostly consists of signals from slowly-moving tissue (e.g. in the case of the FloWire, this typically involves vessel wall motion);

gating (or packeting) is used to sample and integrate the Doppler signal over one particular distance range, providing the gated IQ signal. By increasing the gate length (or duration), the Doppler signal is integrated over a longer depth range, increasing the signal-to-noise ratio (SNR) of the Doppler signal at the cost of spatial resolution. The optimal gate duration equals the transmitted pulse duration, as this maximizes the SNR: longer gates do not further improve the SNR. The Doppler spectrum can be estimated by fast Fourier transform (FFT) over a gated IQ signal. The magnitude or power of the Doppler spectrum is calculated (the phase spectrum is typically not used).

Figure 3:
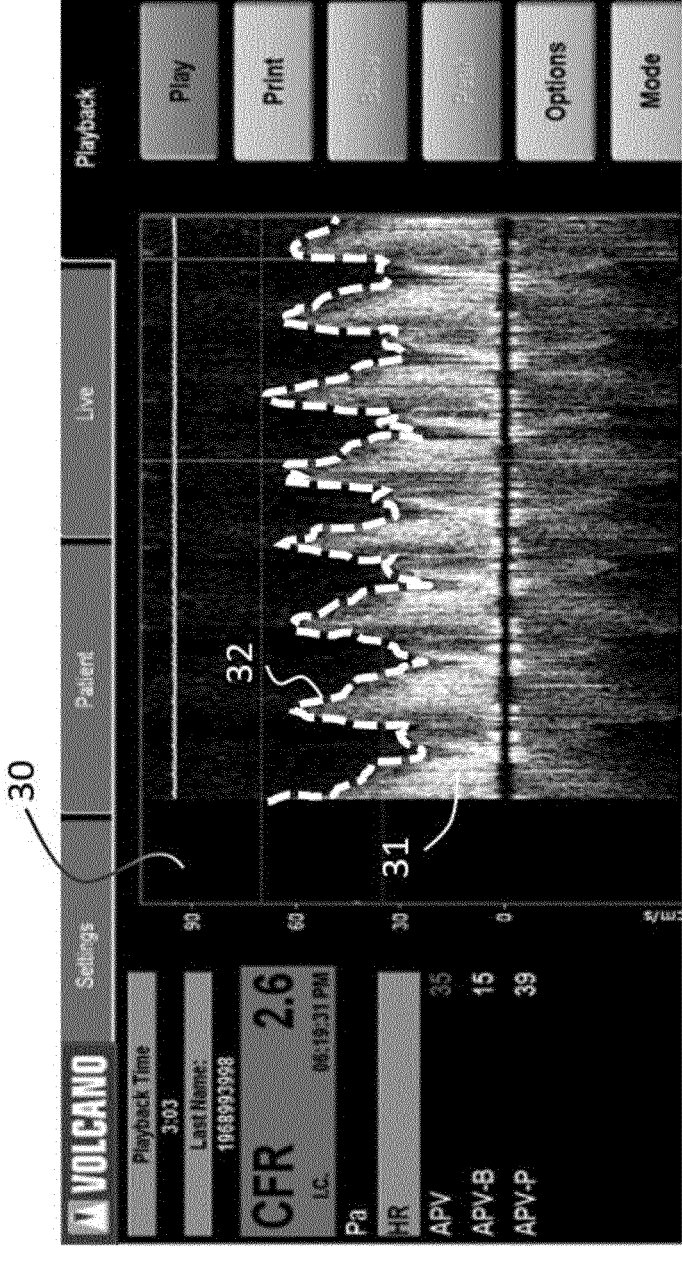
FIG. 3 shows an example of a flow measurement displayed on a user interface.

FIG. 3 shows an example of the velocity that is determined by using an interventional device such as the FloWire, with a pulsed ultrasound Doppler method such as spectral Doppler. This method dynamically estimates the distribution of flow velocities 30 in the sample area 3 as function of time. As such, it does not provide the flow or the flow velocity directly, but rather a distribution of all flow velocities present within the sampling volume, so the measurement provides a lot of information that needs to be summarized to facilitate clinical decision-making. To do so, the entire velocity distribution is characterized by a dynamic flow velocity feature (DFVF).

For the intravascular flow velocity measurement, the instantaneous peak velocity (IPV) is adopted as DFVF, which is illustrated as dashed line 32.

This is based on the idea that, in any blood vessel, flow velocities will be present in a distribution between zero and the IPV. Typically, the highest flow velocities are present in the center of the vessel, while the flow velocity tends to zero when nearing the vessel wall. Accordingly, there will be a clear change in the velocity distribution around the IPV from a significant value to zero. Depending on the signal-to-noise ratio, in the Doppler spectrum, there will be change from a signal spectrum magnitude to the noise floor. The brightness of the area 31 under the dashed line 32 indicates the density of the velocity distribution. As long as the interventional device, e.g. FloWire, is positioned such that its sampling volume 3 includes the location where the flow velocity is highest, such as in FIGS. 2 and 5, the change is clearly identifiable from the detected velocity distribution. In some embodiments the IPV values may be averaged over time (e.g. across a predetermined number of heart cycles) to derive the average peak velocity (APV).

In various other applications, other DFVFs are estimated, e.g. the instantaneous mean velocity (i.e. mean of the instantaneous velocity distribution), which is commonly used in ultrasound color flow imaging (Color Doppler). In Power Doppler, the total power is used as DFVF, which is less quantitative but more sensitive. Another alternative DFVF is the power velocity integral, since this can be estimated more efficiently without first having to estimate the complete velocity distribution. However, the average flow velocity depends very much on the position of the transducer within the vessel, which is difficult to control and to keep stable, and therefore the average flow velocity as measured is highly irreproducible. In ultrasound power Doppler, the presence of flow is shown by just calculating the total power in the velocity distribution (i.e. without calculating any velocity).

Figures 4, 5:
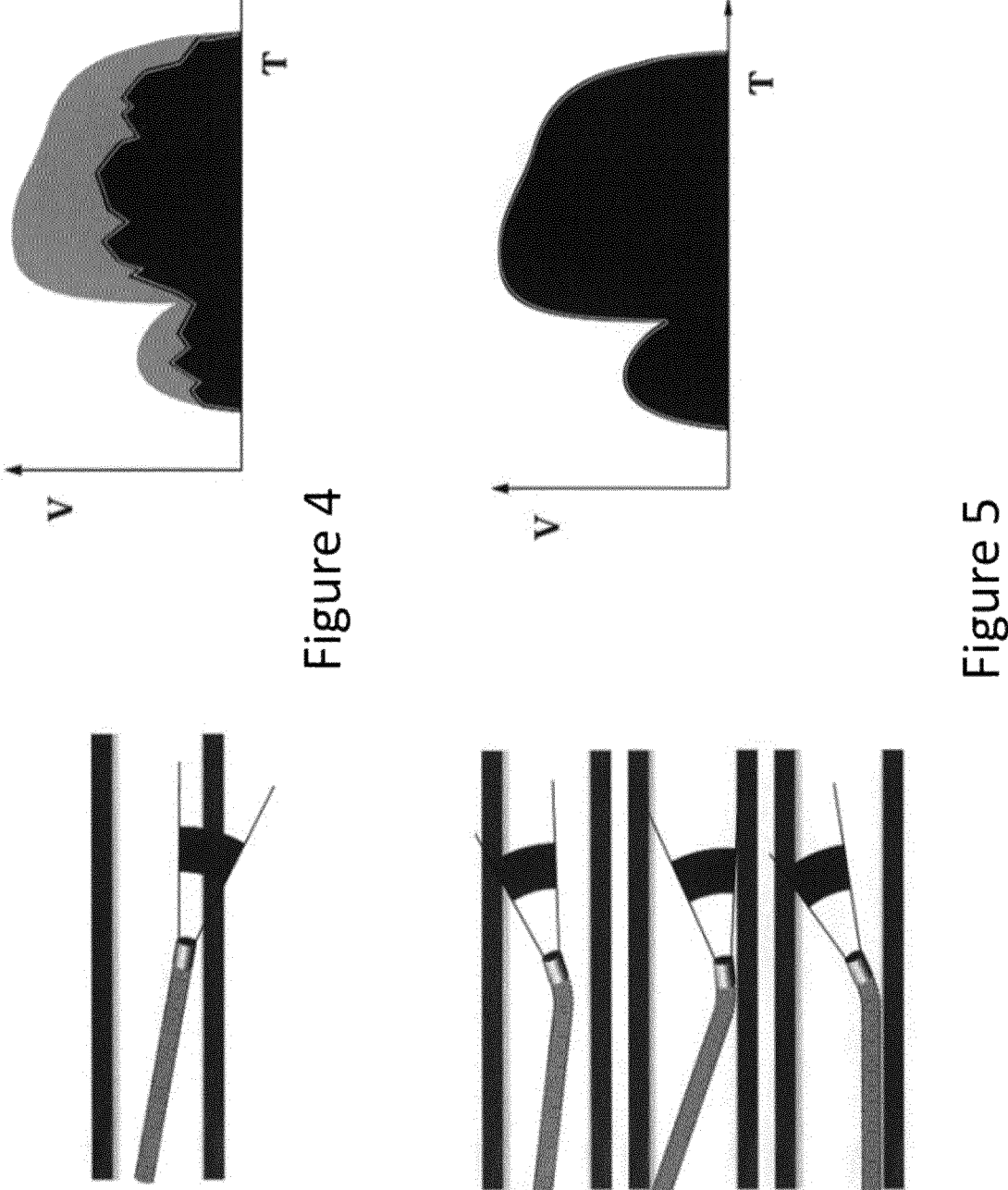
FIG. 4 shows exemplarily a situation of improper orientation of the interventional device for flow measurements in the vessel.
FIG. 5 illustrates exemplarily situations for proper orientation of the interventional device for flow measurement in the vessel.

One of the difficulties with the intravascular spectral Doppler method is the generally limited SNR and robustness of the measurement. This may lead to inaccurate and inconsistent results, in particular when the interventional device, such as FloWire, is not optimally positioned within the vessel. Such an example is shown in FIG. 4. Misalignment of the distal tip of the interventional device in the vessel may lead to suboptimal sampling of the highest velocities in the vessel. This can lead to a suboptimal signal-to-noise ratio, which will make peak velocity calculation more difficult, or even impossible if the sampling area or volume does not contain the highest velocities. Considering that the location and/or orientation of the tip of the interventional device can vary dynamically during a measurement, especially in coronary arteries, which are located in the beating heart, this misalignment can make it difficult to obtain a reliable peak velocity signal. Situations leading to more reliable flow measurements are illustrated in FIG. 5, wherein the sampling volumes comprise the central region of the vessel lumen.

The signal quality of Doppler spectra can further be improved. As mentioned previously, gating is performed to boost the SNR, with the optimal gate length/duration given by the transmitted pulse length. Any further improvement in SNR, by extending the gate length, would thus require a longer transmitted pulse length (e.g. by an increased number of cycles). If one would however transmit a longer pulse, one would in practice need to decrease the transmitted pulse amplitude in order not to exceed ultrasound safety regulations (in particular, the time-averaged acoustic energy). Additionally, a longer transmitted pulse would increase the period while the transducer is transmitting and therefore not being able to be used to receive ultrasound signals.

In the spectral Doppler images, like shown with 30 in FIG. 3, each pixel is calculated as the magnitude spectrum of a complex number (the Doppler signal strength corresponding to a certain Doppler frequency) of which real and imaginary parts are distorted by additive white (Gaussian) noise with mean 0 (in case of noise) and standard deviation $\sigma$. The resulting magnitude is characterized by a Rayleigh distribution (with parameter $\sigma$) that has a mean $\sigma\sqrt{\pi/2}$ and a standard deviation $\sigma\sqrt{(4-\pi)/2}$. This specific form of noise is not limiting, it serves here as an example.

Two correlation effects can be mathematically exploited as follows:

on the relatively short distance scale, the Doppler signal is averaged in the time domain, which reduces the standard deviation $\sigma$ by a factor proportional to the square root of the duration (K) over which the signal is averaged ($\sigma/\sqrt{K}$);

on the relatively long distance scale, the Doppler magnitude spectrum can be averaged across different distance ranges. Since the Doppler magnitude spectra are obtained from distinct locations, i.e. independently, the noise across different distance ranges is uncorrelated. As such, averaging will not affect the mean, but will reduce the standard deviation. For equally distributed signals (with equal variances across distance range), the variance of the combined spectrum is reduced by the square root of the number of distance ranges (N) over which the Doppler magnitude spectrum is averaged. If there is a difference in variances across different distance ranges, the amount of variance reduction achieved by averaging across distance ranges will be lower. This results in a combined effect where the noise level will have a mean $$\sigma\sqrt{\frac{\pi}{2K}}$$

and standard deviation $$\sigma\sqrt{\frac{4-\pi}{2KN}}.$$

The added benefit of combining the Doppler magnitude spectra across different depth ranges is therefore a reduction in the standard deviation by $\sqrt{N}$ in Doppler images. The net result is an increase in the homogeneity of the spectral Doppler images, which provides a clearer contrast between signal and noise.

Figure 6:
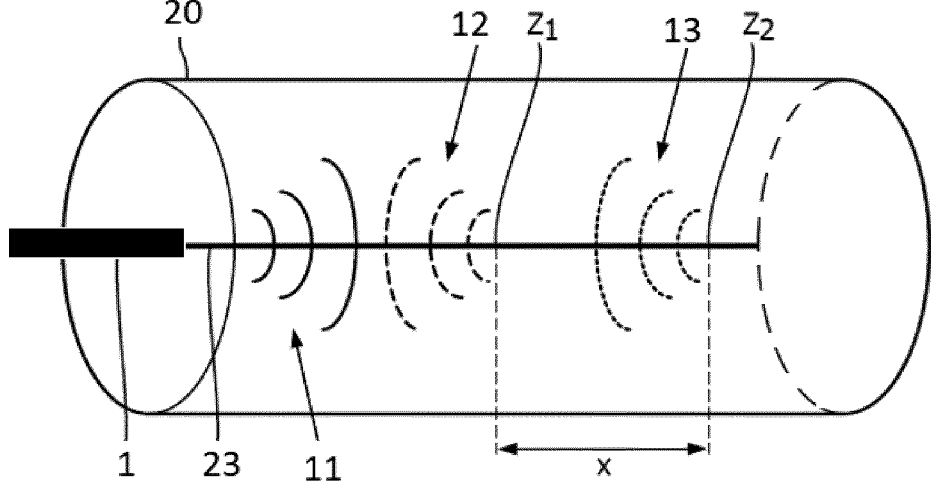
FIG. 6 shows a schematic representation of flow measurement in a vessel.

FIG. 6 shows schematically the interventional device 1 used for measurement of flow within a vessel. Although the interventional device is aligned in the schematic illustration with the central axis 23 of the vessel 20, this is not required, since it is sufficient to have a first ultrasound signal 12 associated to ultrasound reflections at a first location ($z_1$) from the transducer and a second ultrasound signal 13 associated to ultrasound reflections at a second location ($z_2$) from the ultrasound transducer. The ultrasound transducer generates a plurality of ultrasound pulses 11 and receives a plurality of echo signals 12 from a first measurement location, at a first distance $z_1$ from the device, and a plurality of echo signals 13 from a second measurement location, at a second distance from the device. The plurality of echo signals 12 from the first measurement location are used to form a first Doppler signal and the plurality of echo signals 13 from the second measurement location are used to form a second Doppler signal. In an embodiment the first and second locations are spatially aligned along the ultrasound transmission and/or reception axis of the ultrasound transducer. The first and second locations are separated by distance x.

Figure 7:
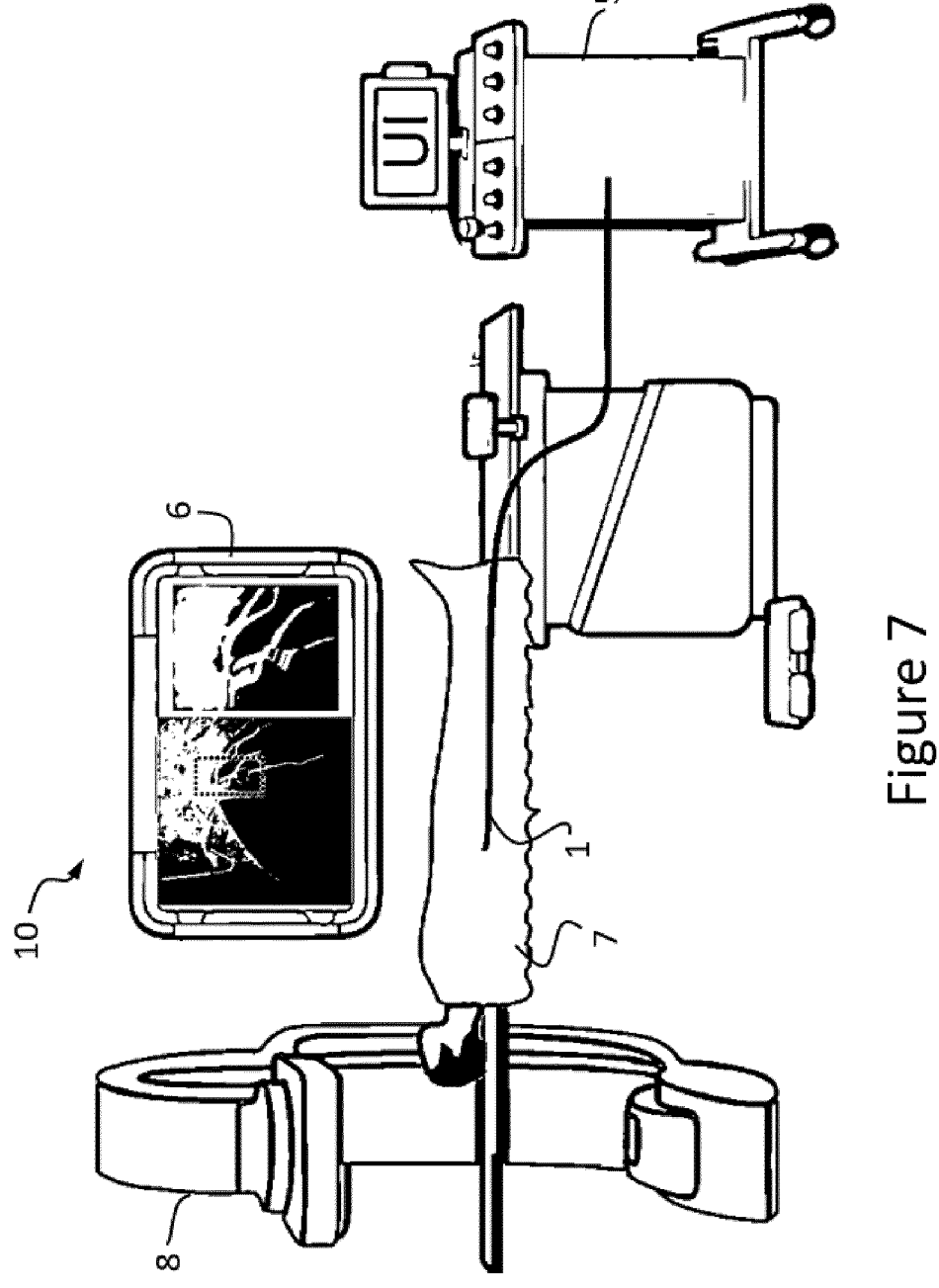
FIG. 7 shows exemplarily embodiments of systems for flow measurement.

The interventional device 1 is connected by wired or wireless connection to an apparatus 5, e.g. a console, as illustrated in FIG. 7. The console may provide the electrical excitation pulse to the ultrasound transducer. Alternatively, the electrical excitation pulse could be provided by an autonomous electrical component that is integrated in the proximal portion of the interventional device, wherein the proximal portion of the interventional device remains outside of the body of the patient 7 during flow measurement with the distal portion of the interventional device inserted into the anatomical structure of the patient. In a further alternative the electrical source is integrated in the proximal portion of the interventional device and is configured to communicate with an application specific integrated circuit (ASIC) located nearby the ultrasound transducer in the distal portion of the interventional device, which ASIC provides then the electrical excitation pulses for the ultrasound transducer. Optionally, the measurement data can be transmitted wirelessly directly to a user interface such as a display 6. In any of the embodiments a processor is involved in processing the measurement data to output the result of the flow measurement. The processor may be integrated in at least one of: the console, the display and the proximal portion of the interventional device (e.g. handset). The measurement result may be presented on a user interface in the form of a visual representation (e.g. graphical and/or numerical), or it can be presented as acoustic signal, wherein the acoustic characteristics of the signal vary according to the output flow result.

The system 10, schematically illustrated in FIG. 7, may comprise in various alternative configurations the following components:

the interventional device wherein the processor is integrated within the proximal portion of the interventional device, further comprising a user interface for outputting the flow results, and wherein the processor communicates through wireless communication with the user interface;

the interventional device in wired or wireless communication with a console that comprises the processor, and which outputs the flow result to the user interface, which user interface can be separate from or integrated in the console.

In any of the embodiments, the system may further comprise at least an extracorporeal apparatus 8 suitable for providing at least one of the imaging modalities: x-ray angiography, computer tomography, ultrasound imaging and magnetic resonance imaging.

Figure 8:
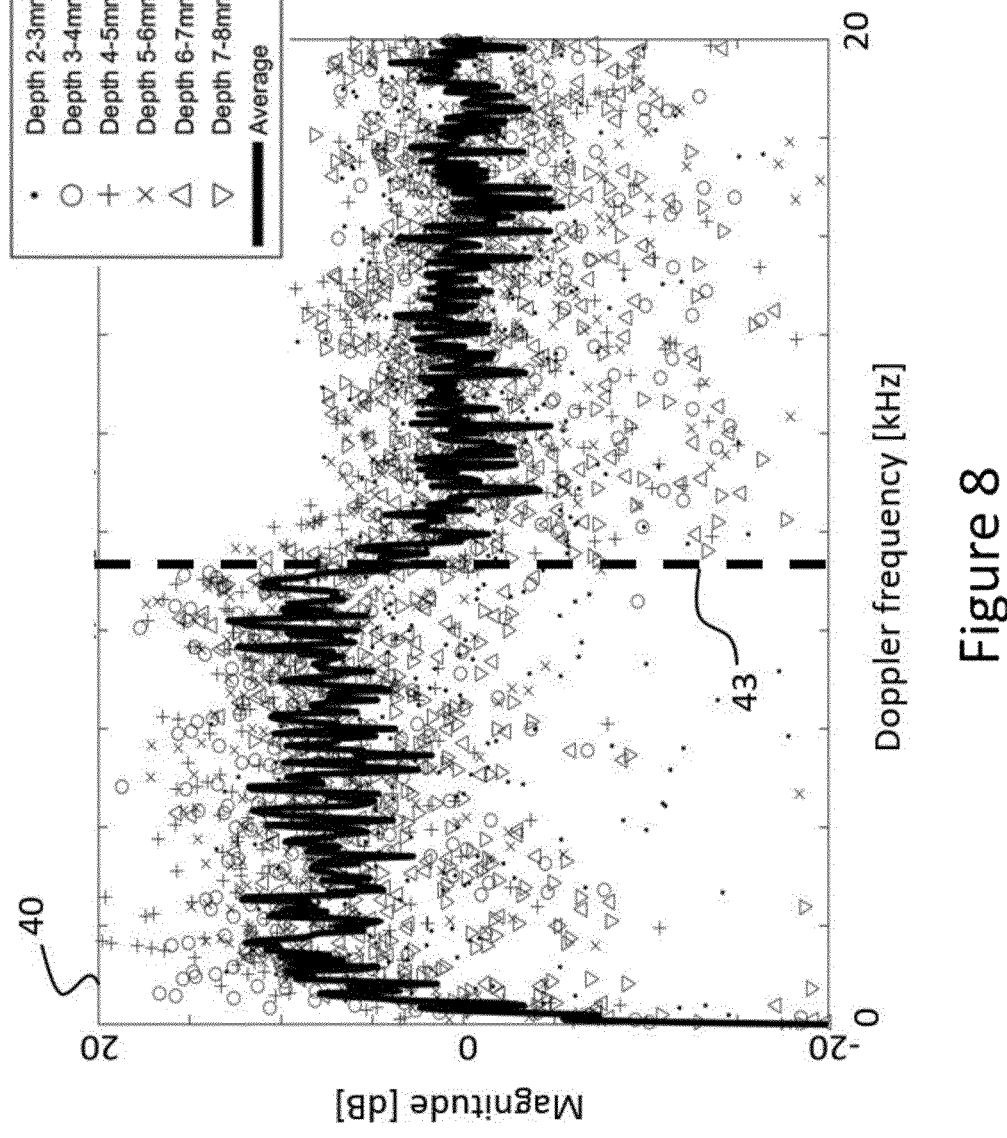
FIG. 8 shows Doppler magnitude spectra at various measurement depths.
Figure 9:
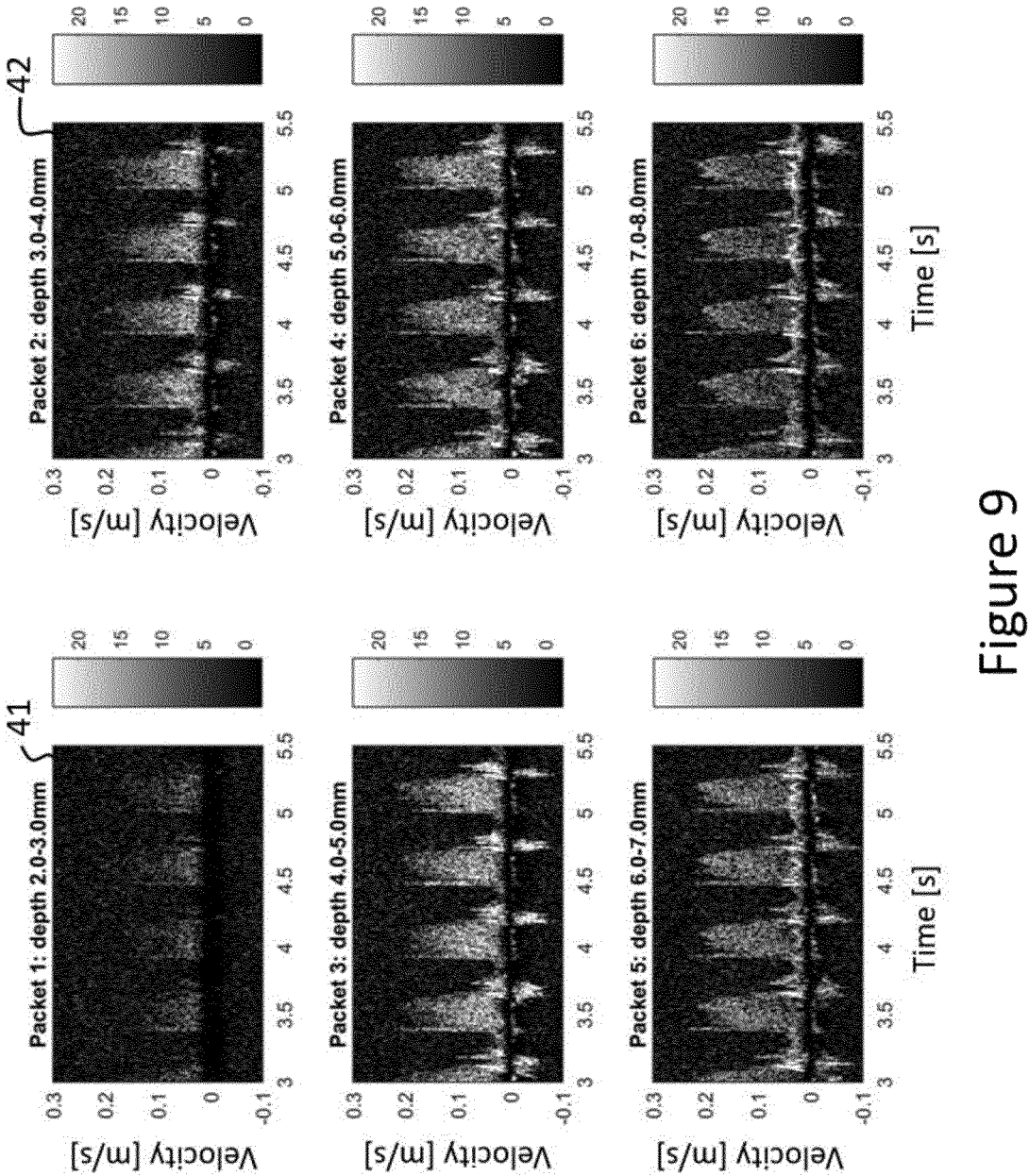
FIG. 9 shows grayscale coded Doppler spectra at various depth intervals as function of time, obtained in-vivo.
Figure 10:
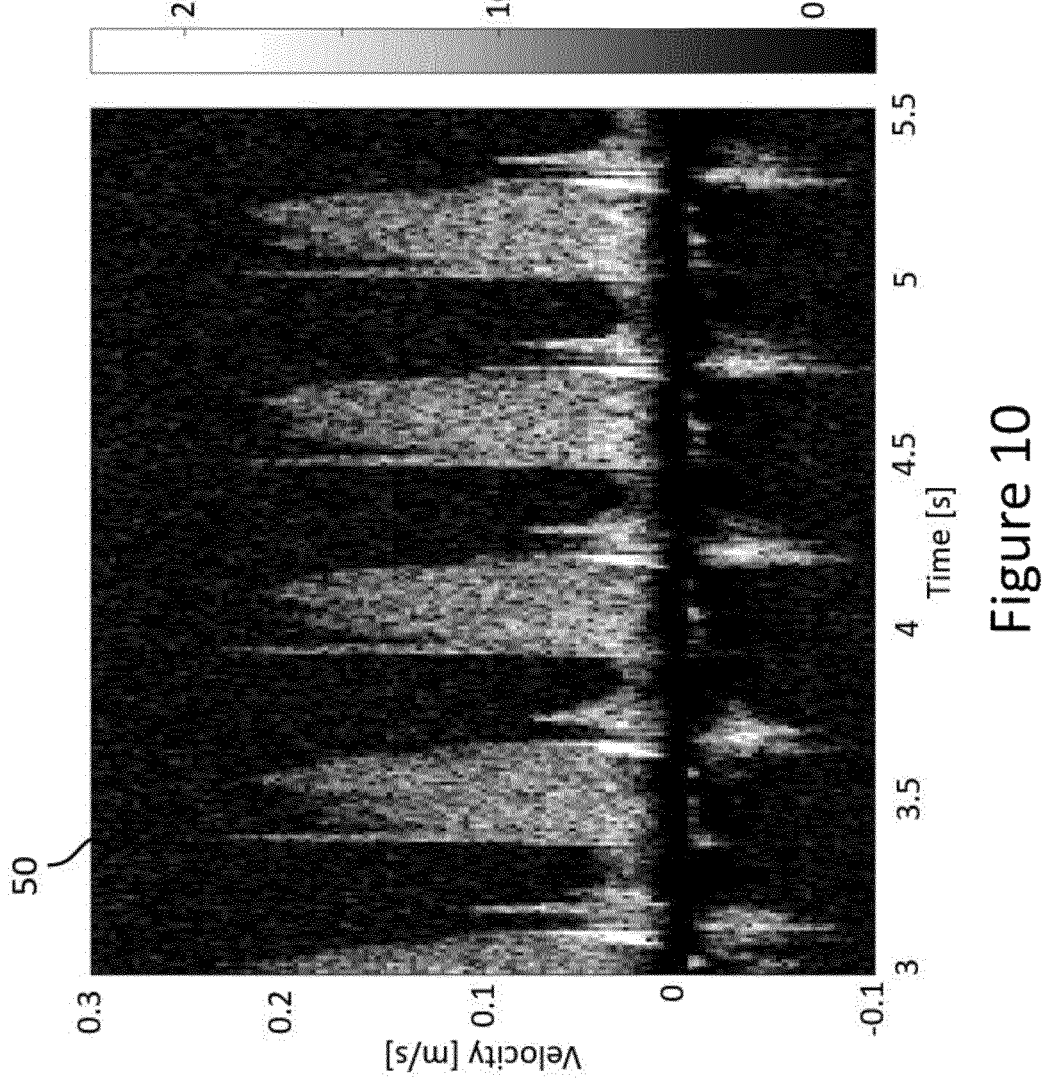
FIG. 10 shows composite Doppler spectrum obtained by averaging the spectra shown in FIG. 9.

An example of in-vivo measured Doppler spectra sampled simultaneously at different depth ranges is shown in the graphical representation 40 of FIG. 8. It is to be noted that by averaging magnitude spectra obtained at different depth ranges, the variance of both Doppler signal and noise floor can be reduced. This results in an increased homogeneity and therefore an increased contrast between signal and noise. The visualization of the effect can further be observed by comparing the graphical representations of the Doppler spectra for various distance ranges (e.g. 41,42) from FIG. 9 with the graphical representation in FIG. 10. In this particular example, a simple average of the Doppler magnitude spectra (prior to conversion to dB) is used, i.e. an arithmetic average, to compute the composite Doppler spectrum 50 as shown in FIG. 10, after scaling the different Doppler spectra per distance range, such that the noise floor was equal. There are several advanced options that can be considered in alternative embodiments for combining the information from the individual Doppler spectra per associated depth intervals (or ranges), such as geometric mean, median, etc. In some embodiments instead of using individual Doppler spectra obtained from subsequent distance ranges, whether adjacent to each other or not, overlapping distance ranges can be considered (e.g. 2-3 mm, 2.5-3.5 mm, 3-4 mm, . . . ) for the computation of the composite Doppler spectrum.

In some embodiments, means are provided for selecting and/or weighting the distance ranges over which the Doppler magnitude spectra are combined. This is beneficial since not all magnitude spectra for the different distance ranges comprise exactly the same velocity distribution. The weighting, which in case of binary weights is equivalent to selection of the distance ranges, can be based on several inputs. Weighting/selection can be done dynamically by the processor or can be determined by the user of the system through indicating the weights that it wants to associate to Doppler spectra belonging to certain distance ranges or through selecting the desired distance ranges on the user interface that are then considered for computation of the composite Doppler spectrum. Weights can vary as function of the distance range, time, and Doppler frequency.

In some embodiments prior assumptions can be used, such as for example the type of clinical application. The configuration of the measurement system in which the flow-sensing interventional device (e.g. guidewire) is inserted into a blood vessel, may have some consequences on the flow velocity profile in the vessel. In particular, the presence of the guidewire disturbs the flow velocity profile close to its distal tip, such that the axial velocities measured at distance ranges in close proximity to the distal tip are somewhat lower than those measured at further distance ranges. The distance for which this effect is significant depends on the vessel diameter and on the flow. Based on this, distance ranges in the close proximity of the distal tip of the interventional device (e.g. closer than 2 mm) could be ignored or a low value of weighting factor can be associated for computing the composite Doppler magnitude spectrum. For example, a reduced weight can be attributed to distance ranges in the close proximity of the distal tip compared to Doppler spectra associated to distance intervals located further away from the distal tip of the interventional device. In additional or alternative embodiments, distal ranges that are too far from the ultrasound transducer and at which the usable Doppler signal is of too low quality, can similarly be ignored or the Doppler spectra belonging to those distance ranges can be associated a low value of weighting factor. This is advantageous due to finite penetration depth of ultrasound waves in the measured medium (e.g. blood or tissue) which is ultrasound frequency dependent, and hence the contribution of the respective distance ranges can be minimized or ignored. Furthermore, the ultrasound beam diverges with penetration depth, unless it is focused ultrasound beam, and at certain penetration depth the ultrasound beam becomes broader than the vessel diameter, and the contribution of the distance intervals around and beyond that particular penetration depth adds only clutter to the measurement and little to no usable velocity signal. Focusing ultrasound beam for ultrasound transducer on interventional devices such as guidewire or interventional needle is problematic because of their cross sectional dimension, in special when the ultrasound transducer is integrated at the distal end of the interventional device.

Figure 11:
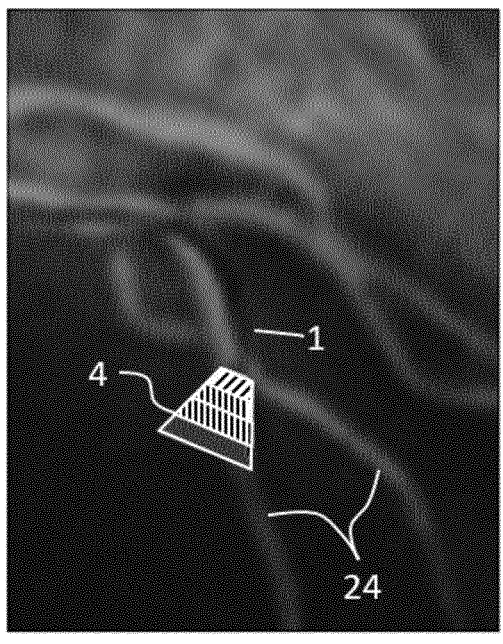
FIG. 11 is an angiogram showing the vessels, the flow-sensing interventional device, and the flow measurement field.
Figure 12:
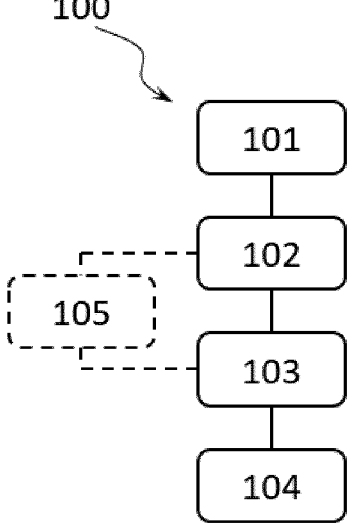
FIG. 12 illustrates exemplarily a method of flow measurement.

In a further alternative embodiment, imaging modality (e.g. angiography) can provide insights into how well the flow velocity profile (inside the vessel) is covered for different distance ranges. Angiography can be used in combination with a Vessel Navigator, as shown in FIG. 11. The information about the distances that are optimal for measurement of flow can be provided to the processor of any of the system embodiments disclosed in relation to FIG. 7, upon which the processor provides an automated optimization of weighting of the Doppler spectra for various distance ranges for the computation of the composite Doppler spectrum. The interventional device can be presented as imaged by the imaging system at location within the vessel such as in FIG. 11. Additionally or alternatively, the interventional device may be navigated to the desired location of measurement. Co-registration can be used to track the distal region of the interventional device with respect to the morphology of the vessel obtained from the imaging system (e.g. by use of radiopaque marker on the interventional device or by electromagnetic tracking of a coil in the distal portion of the device). In some embodiments the processor may be configured to automatically zoom in at the location of the distal portion of the interventional device, while the flow measurement is not started. In some embodiments the distal portion of the interventional device is emphasized in the presented image. In other embodiments the distal portion of the interventional device and the vessel anatomy are both enhanced in the presented image. In some embodiments the measurement field 4 of the ultrasound transducer is visualized with respect to the vessel anatomy (e.g. wall). The ultrasound measurement field or the ultrasound transducer beam profile may be known from fabrication and calibration measurements of ultrasound transducers that are integrated into the interventional devices. The ultrasound measurement field or the ultrasound transducer beam profile may depend on frequency and excitation pulse and may have been implemented as recorded into a library stored on a memory device. By coupling a particular interventional device for measurement, the processor automatically selects the corresponding ultrasound measurement field or ultrasound transducer beam profile from the library and overlays it on the image comprising the vessel anatomy and the interventional device. Further in some embodiments, the processor may be configured to allow flow measurement only if the ultrasound measurement field or the ultrasound transducer beam profile does not intersect the vessel walls. In further embodiments the processor is configured to automatically select the distance intervals for the sampling ranges based on the distance intervals within the ultrasound measurement field or ultrasound transducer beam profile that are within the lumen of the vessel with a predetermined lateral distance from the vessel wall. In yet further embodiments the processor may be configured to output the ultrasound measurement field or the ultrasound transducer beam profile onto the display differently when the location and/or orientation of the ultrasound measurement field with respect to the vessel wall is suitable for flow measurement than in the situation when the circumstances would not allow reliable flow measurements. In an example the suitable and less suitable circumstances for flow measurements may be presented with different colors, e.g. green for suitable conditions and orange to red for less suitable circumstances. Optionally, the ultrasound measurement field or ultrasound beam profile may be represented differently for distance intervals suitable or less suitable for flow measurement (e.g. hatched or colored). In an alternative, the interventional device can be presented in the context of Dynamic Coronary Roadmap, such as described particularly related to FIGS. 1 and 2 of Piayda et al. Eur J Med Res (2018) 23:36 (https://doi.org/10.1186/s40001-018-0333-x).

Alternatively, besides or instead of x-ray angiography, other imaging modalities that are capable of providing anatomic information together with position and/or orientation information of the interventional device can be used in the system. Imaging systems 8 are herein contemplated, which are providing ultrasound imaging, magnetic resonance imaging (MRI) or computer tomography (CT). These imaging modalities may provide three-dimensional (3D) information to better assess the orientation of the flow velocity measurement field 4 of the ultrasound transducer in conjunction with the anatomic structure, e.g. the blood vessels 24. Alternatively or additionally, the position and/or orientation of the distal tip of the interventional device 1 may be tracked with ultrasound localization techniques or by optical fibers integrated within the interventional device, as known by the person skilled in the art from the patent literature.

In some embodiments the selection and/or weighting of the Doppler magnitude spectra can be based on the content of the spectra themselves (i.e. data-driven). This can be implemented in various ways:

general data-adaptive methods can be adopted to optimally exploit the correlation among Doppler magnitude spectra obtained at different distance ranges. Weights can be based on actual correlation among the magnitude spectra measured at different distance ranges;

adaptive algorithms can be used to determine weights that optimize a certain cost function, e.g. minimum variance of the combined Doppler magnitude spectrum;

selection and/or weights can be determined with the purpose to optimize the accuracy of DFVF estimation. Weights for the different distance ranges could be determined based on how much the Doppler magnitude spectrum of a particular distance range contributes to the accuracy of DFVF estimation, for example if a Doppler magnitude spectrum at a certain distance range will contain only noise, this contribution will be negative and it is preferable not to take this distance range into account in the DFVF estimation. To show how this approach could be implemented, the IPV as an example DFVF is used and the gradient of the Doppler magnitude spectrum at the IPV as the feature is used to measure the contribution of a distance range to the DFVF estimation. As shown in the example Doppler magnitude spectrum of FIG. 8, there is a significant negative gradient in the magnitude spectra between 8 and 10 kHz, i.e. in the frequency range corresponding to the IPV tracing 43. The strength of this gradient is a measure for how accurately the IPV can be estimated. Alternatively, other features such as SNR may be used for this purpose. As such, an algorithm for iterative optimization of weights can be used (starting e.g. from unity weights), comprising: calculation of the weighted combined magnitude spectrum; estimation of the IPV; testing whether the IPV is sufficiently accurate: if yes then stop, if not then continue to calculation of gradient in IPV for all magnitude spectra; updating weights for all magnitude spectra based on gradient and go back to the first step of calculation of the weighted combined magnitude spectrum. The confidence with which the IPV is estimated depends on the difference in intensity between the desired blood flow signal and the noise floor. In an embodiment, this confidence may be quantified by the difference or gradient in the Doppler magnitude spectrum over frequency at the detected IPV. One may evaluate to what extent the individual Doppler magnitude spectra contribute to the difference or gradient of the composite Doppler magnitude spectrum, and optimize the weights such that this difference or gradient is maximized. This optimization may be implemented as an iterative process in which weights are initialized (e.g. unity weights). The iterative process starts by calculating the composite Doppler magnitude spectrum. Next, the IPV is evaluated and the difference or gradient of the individual magnitude spectra at the IPV is evaluated. The weights are optimized based on the difference or gradient values, and the iterative process goes back to its start. The iteration process may stop whenever a satisfactory difference or gradient value of the composite Doppler magnitude spectrum is found, when the increase in this difference or gradient value is below a threshold, when the absolute or relative change in IPV is below a threshold, when the weights hit upper/lower limit of allowed values, when a local optimum is found given a certain step size, or when a maximum number of iterations is reached.

In any of the embodiments of the interventional device the ultrasound transducer may include a number of ultrasound transducer elements, in which case, the ultrasonic pulses may be directed to comprise sampling volumes from the central region of the vessel lumen with maximum flow velocity by using electronic beam steering and/or electronic beam focusing. In this way, the measurements may be made less sensitive to the orientation of the interventional device. In some embodiments of the system electronic beam steering and focusing may be applied so as to optimally align the ultrasound beam with the flow direction. The ultrasound beam angle can be optimized to maximize the strength of the Doppler signal. Optimization of the beam angle may be performed in an iterative and/or adaptive manner. Any of the transducers of the interventional device may be conventional ultrasound transducers comprising PZT or PVDF, or may be micromachined ultrasound transducers (capacitive or piezoelectric).

In a further aspect of the invention a method 100 of flow measurement is provided, comprising:

obtaining 101 a first ultrasound signal and a second ultrasound signal from an ultrasound transducer of an interventional device, wherein the first ultrasound signal is associated to ultrasound reflection at a first location at a first distance from the ultrasound transducer and the second ultrasound signal is associated to ultrasound reflection at a second location at a second distance from the ultrasound transducer;

ascertaining 102 a first flow parameter at the first location and a second flow parameter at the second location;

ascertaining 103 a composite flow parameter based on the first flow parameter and the second flow parameter;

outputting 104 to a user interface the composite flow parameter.

The method may comprise in optional embodiments the processor carrying out operations that are mentioned for any of the embodiments of the apparatus according to the invention, for example as an option applying 105 various weighting factors to the contribution of the Doppler spectra of various distance ranges for the computation of the composite Doppler spectrum.

Further, a computer program comprising code means is provided, which when run on a computer, implements any of the methods according to the invention on any of the systems to output a composite flow parameter, e.g. composite Doppler spectrum, instantaneous peak velocity, average peak velocity. The computer program may be stored/distributed on a suitable medium, such as an optical storage medium or a solid-state medium, supplied together with or as part of other hardware, but may also be distributed in other forms, such as via the Internet or other wired or wireless telecommunication systems.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An apparatus for flow measurements in a vessel, comprising a processor configured to:

obtain a first ultrasound signal and a second ultrasound signal from an ultrasound transducer of an interventional device, wherein the ultrasound transducer is positioned at a location within the vessel and generates a plurality of ultrasound pulses, wherein the first ultrasound signal is associated to ultrasound echoes that reflect from a first location $(z_1)$ within the vessel in response to the plurality of ultrasound pulses, and the second ultrasound signal is associated to ultrasound echoes that reflect from a second location $(z_2)$ within the vessel in response to the plurality of ultrasound pulses, wherein the first location and the second location are separate from the location of the ultrasound transducer, wherein a first distance interval is between the first location and the location of the ultrasound transducer, and a second distance interval is between the second location and the location of the ultrasound transducer, wherein the first distance interval and the second distance interval are spatially aligned along an ultrasound transmission and/or reception axis of the ultrasound transducer;

determine a first flow parameter at the first location based on the first ultrasound signal, and a second flow parameter at the second location based on the second ultrasound signal;

determine a composite flow parameter based on the first flow parameter and the second flow parameter; and output, to a user interface, the composite flow parameter.

2. The apparatus of claim 1, wherein the first distance interval second distance interval are adjacent distance intervals along the ultrasound transmission and/or reception axis of the ultrasound transducer.

3. The apparatus of claim 1, wherein the first and second distance interval partially overlap.

4. The apparatus of claim 1, wherein the first flow parameter and the second flow parameter individually comprise at least one of a Doppler magnitude spectrum, a Doppler power spectrum, an instantaneous peak velocity, and an average peak velocity.

5. The apparatus of claim 1, wherein the processor is configured to determine the composite flow parameter based on a first weighting factor applied to the first flow parameter and a second weighting factor applied to the second flow parameter.

6. The apparatus of claim 5, wherein the first and second weighting factors are ascertained automatically by the processor.

7. The apparatus of claim 6, wherein the weighting factors are ascertained based on correlation among the Doppler magnitude spectra for the respective distance intervals, preferably based on optimization by using minimum variance of the combined Doppler magnitude spectrum over the distance intervals.

8. The apparatus of claim 6, wherein the weighting factors are ascertained based on the gradient of the Doppler magnitude spectra for the respective distance intervals.

9. The apparatus of claim 6, wherein the processor is configured to receive position and/or orientation information of the ultrasound transducer with respect to an anatomy of the vessel for which the flow measurement is performed, wherein the position and/or orientation information defines the ultrasound transmission and/or reception axis of the ultrasound transducer, and wherein the processor is further configured to ascertain the first and second weighting factors based on the position and/or orientation information.

10. The apparatus of claim 1, wherein processor is configured to determine the composite flow parameter based on an average of Doppler magnitude spectra after scaling individual ones of the Doppler magnitude spectra for the first distance interval and the second distance interval such that noise floor values over the first distance interval and the second distance interval are brought to substantially equal values.

11. The apparatus of claim 1, wherein determining the composite flow parameter includes (i) determining a geometric mean of the first flow parameter and the second flow parameter, and/or (ii) determining an average of the first flow parameter and the second flow parameter.

12. A system for flow measurements in a vessel, comprising:

a processor configured to:

obtain a first ultrasound signal and a second ultrasound signal from an ultrasound transducer of an interventional device, wherein the ultrasound transducer is positioned at a location within the vessel and generates a plurality of ultrasound pulses, wherein the first ultrasound signal is associated to ultrasound echoes that reflect from a first location ($z_1$) in response to the plurality of ultrasound pulses, and the second ultrasound signal is associated to ultrasound echoes reflect from a second location ($z_2$) in response to the plurality of ultrasound pulses, wherein the first location and the second location are separate from the location of the ultrasound transducer, wherein a first distance interval is between the first location and the location of the ultrasound transducer, and a second distance interval is between the second location and the location of the ultrasound transducer, wherein the first distance interval and the second distance interval are spatially aligned along an ultrasound transmission and/or reception axis of the ultrasound transducer;

ascertain a first flow parameter at the first location based on the first ultrasound signal, and a second flow parameter at the second location based on the second ultrasound signal;

ascertain a composite flow parameter based on the first flow parameter and the second flow parameter; and output, to a user interface, the composite flow parameter;

the interventional device including the ultrasound transducer on a distal portion of the interventional device; and the user interface for outputting the composite flow parameter.

13. A method of flow measurement in a vessel, comprising:

obtaining a first ultrasound signal and a second ultrasound signal from an ultrasound transducer of an interventional device, wherein the ultrasound transducer is positioned at a location within the vessel and generates a plurality of ultrasound pulses, wherein the first ultrasound signal is associated to ultrasound echoes that reflect from a first location ($z_1$) within the vessel in response to the plurality of ultrasound pulses, and the second ultrasound signal is associated to ultrasound echoes that reflect from a second location ($z_2$) within the vessel in response to the plurality of ultrasound pulses, wherein the first location and the second location are separate from the location of the ultrasound transducer, wherein a first distance interval is between the first location and the location of the ultrasound transducer, and a second distance interval is between the second location and the location of the ultrasound transducer, wherein the first distance interval and the second distance interval are spatially aligned along an ultrasound transmission and/or reception axis of the ultrasound transducer;

determining a first flow parameter at the first location and a second flow parameter at the second location based on the first and second ultrasound signals, respectively;

determining a composite flow parameter based on the first
    flow parameter and the second flow parameter; and
outputting, to a user interface, the composite flow param-
    eter.

\* \* \* \* \*